United States Patent
Endrizzi et al.

(10) Patent No.: US 9,952,163 B2
(45) Date of Patent: Apr. 24, 2018

(54) CODED-APERTURE X-RAY IMAGING

(71) Applicant: UCL BUSINESS PLC, London (GB)

(72) Inventors: Marco Endrizzi, London (GB); Alessandro Olivo, London (GB); Paul Diemoz, London (GB); Thomas Millard, London (GB); Fabio Vittoria, London (GB)

(73) Assignee: UCL BUSINESS PLC, London (GB)

( * ) Notice: Subject to any disclaimer, the term of this patent is extended or adjusted under 35 U.S.C. 154(b) by 198 days.

(21) Appl. No.: 14/898,281

(22) PCT Filed: May 29, 2014

(86) PCT No.: PCT/GB2014/051629
§ 371 (c)(1),
(2) Date: Dec. 14, 2015

(87) PCT Pub. No.: WO2014/202949
PCT Pub. Date: Dec. 24, 2014

(65) Prior Publication Data
US 2016/0146744 A1 May 26, 2016

(30) Foreign Application Priority Data
Jun. 21, 2013 (GB) .................................. 1311091.1

(51) Int. Cl.
*G01N 21/00* (2006.01)
*G01N 23/04* (2018.01)
*A61B 6/00* (2006.01)

(52) U.S. Cl.
CPC ............. *G01N 23/04* (2013.01); *A61B 6/484* (2013.01); *A61B 6/5205* (2013.01);
(Continued)

(58) Field of Classification Search
CPC ................ G01N 23/20; G01N 23/207; G01N 23/200091; G01N 2223/056; G01N 23/20008; G21K 1/06; A61B 6/4846
(Continued)

(56) References Cited

U.S. PATENT DOCUMENTS

2010/0327175 A1* 12/2010 Nesterets ............... G01N 23/04
250/393

FOREIGN PATENT DOCUMENTS

GB        2 441 578       3/2008
WO    WO 2013/011317     1/2013

OTHER PUBLICATIONS

Pfeiffer F, et al., "Hard-X-ray dark-field imaging using a grating interferometer", Jan. 13, 2008, published online at http://www.ncbi.nlm.nih.gov/pubmed/18204454, with digital online identifier doi: 10.1038/nmat2096.
(Continued)

*Primary Examiner* — Don Wong
(74) *Attorney, Agent, or Firm* — Leason Ellis LLP

(57) ABSTRACT

A method of X-ray imaging includes passing an X-ray beam through a pre-sample mask 8 with a plurality of apertures 32, through a sample 10, and then through a detector mask 6 with aligned apertures 34. The beams are detected. The detector mask 6 and pre-sample mask 8 are moved with respect to one another to identify the position of maximum intensity and then moved to two further positions on equal and opposite spacings on either side of the maximum. Images are acquired and a transmission image, refraction image and scattering image calculated.

21 Claims, 5 Drawing Sheets

(52) U.S. Cl.
CPC ........... *A61B 6/4035* (2013.01); *A61B 6/4291* (2013.01); *G01N 2223/401* (2013.01); *G01N 2223/612* (2013.01)

(58) Field of Classification Search
USPC .......................................... 378/6, 70, 71, 87
See application file for complete search history.

(56) References Cited

OTHER PUBLICATIONS

P. R. T. Munro et al: "Phase and absorption retrieval using incoherent X-ray sources", Proceedings of the National Academy of Sciences, vol. 109, No. 35, Aug. 13, 2012 (Aug. 13, 2012), pp. 13922-13927, XP055133408, ISSN: 0027-8424, DOI: 10.1073/pnas.1205396109.
Olivo Alessandro et al: "A coded-aperture technique allowing x-ray phase contrast imaging with conventional sources", Applied Physics Letters, American Institute of Physics, US, vol. 91, No. 7, Aug. 16, 2007 (Aug. 16, 2007), pp. 74106-74106, XP012100704, ISSN: 0003-6951, DOI: 10.1063/1.2772193.
Rigon Luigi et al: "Three-image diffraction enhanced imaging algorithm to extract absorption, refraction, and ultrasmall-angle scattering", Applied Physics Letters, American Institute of Physics, US, vol. 90, No. 11, Mar. 13, 2007 (Mar. 13, 2007), pp. 114102-114102, XP012093640, ISSN: 0003-6951, DOI: 10.1063/1.2713147.

\* cited by examiner

CODED-APERTURE X-RAY IMAGING

CROSS-REFERENCE TO PRIOR APPLICATION

The present application is a U.S. national phase application under 35 U.S.C. § 371 of International Patent Application No. PCT/GB2014/051629, filed May 29, 2014, which claims priority to United Kingdom patent application No. 1311091.1, filed Jun. 21, 2013, the disclosures of all of which are hereby incorporated by reference in their entireties. The International Application was published in English on Dec. 24, 2014 as WO 2014/202949.

The invention relates to a method of X-ray imaging and apparatus for carrying out X-ray imaging.

"Coded-aperture" X-ray phase-contrast imaging is based on the edge illumination principle. Edge illumination enables the detection of the phase shifts imparted to an X-ray beam traversing a sample by means of a simple set-up composed of two absorbing edges or slits and a detector. This is adapted to a two-dimensional area imaging set-up by means of apertured masks. An example coded aperture system is presented in WO2013/011317. A first series of apertures is placed in front of the sample and a second series is placed in front of a detector. The pixels on the detector match the projected pitch of the apertures such that typically a one-to-one relationship exists between each aperture and the pixel columns (rows) of the detector, although line-skipping solutions have also been implemented. In that patent, quantitative phase retrieval is demonstrated by using two specific relative positions of sample and detector "coded-aperture" masks.

The X-ray phase-contrast imaging system obtained in this way is robust against the polychromaticity of the beam and can operate with a reasonable focus spot size without requiring any aperturing or collimation of the source.

However, in order for this approach to work the displacement between the masks must be very accurately controlled, to better than pixel accuracy, and aligning masks in this way can be difficult in practice.

A method of X-ray imaging to produce a dark field image is described in Pfeiffer et al, "Hard-X-ray dark-field imaging using a grating interferometer", 13 Jan. 2008, published online at http://www.ncbi.nlm.nih.gov/pubmed/18204454, with digital online identifier doi:10.1038/nmat2096.

However, although the approach described in that paper gives good dark field images it still requires significant dosage, which is not ideal in many applications. Moreover, the alignment is more demanding, exposure times can be longer and a sequence of typically 6-8 "phase stepping" images is required.

There is accordingly a need for an improved dark-field imaging system.

According to the invention there is provided a method of X-ray imaging according to claim 1.

The method extends the approach of WO2013/011317 to provide additionally a dark field image, i.e. an image representing scattering.

The method allows for the capture of X-ray images representing three different aspects of the measured sample. In particular, the method allows for the capture of one or all of an absorption image, a refraction (phase) image and an ultra-small angle scattering (dark field) image.

Further, phase retrieval can be performed to obtain a refraction (phase) image with a more generic relative positioning of the two masks compared with the method as taught in WO2013/011317. In addition, the method taught may substantially relax the tolerance within which one mask needs to be aligned with respect to the other.

One of the masks may be aligned with respect to a maximum to capture one image and then offset to capture another. If required, an equal and opposite offset in the opposite direction may be used to capture a third image. From the three directly measured, captured, images, up to three of the absorption image, the refraction (phase) image and the dark field image may be captured.

The method does not require large doses of X-rays. This is a particular advantage for medical imaging but can have benefits in all applications.

BRIEF DESCRIPTION OF DRAWINGS

For a better understanding of the invention embodiments will now be described, with reference to the accompanying Figures, in which.

DETAILED DESCRIPTION

Figure 1:
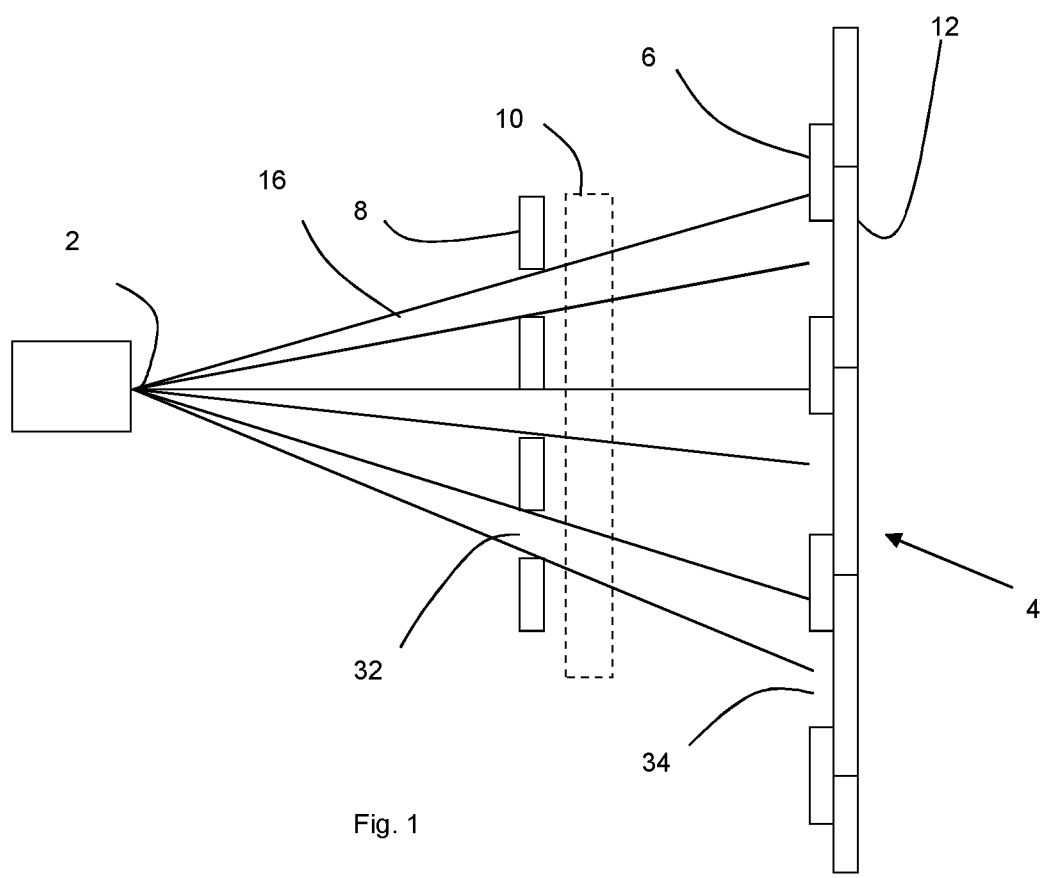
FIG. 1 shows apparatus according to an embodiment of the invention.
Figure 2A:
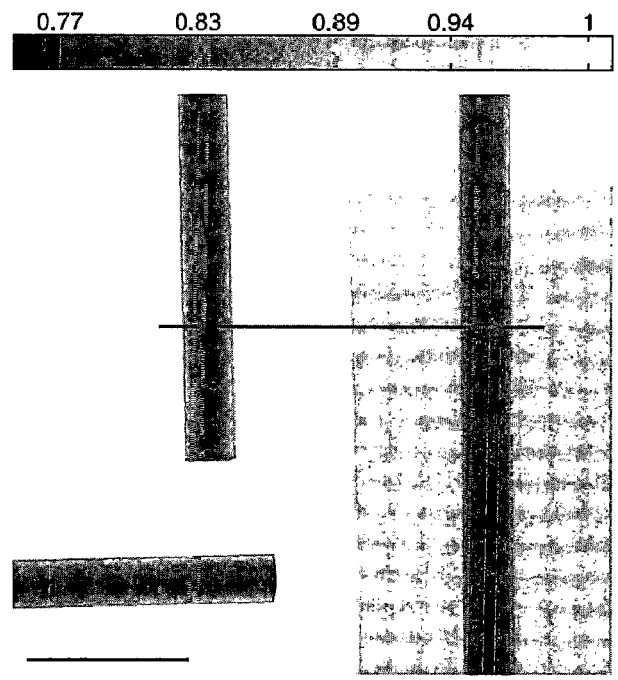
FIG. 2 shows images captured in accordance with an embodiment of the invention.
Figure 2D:
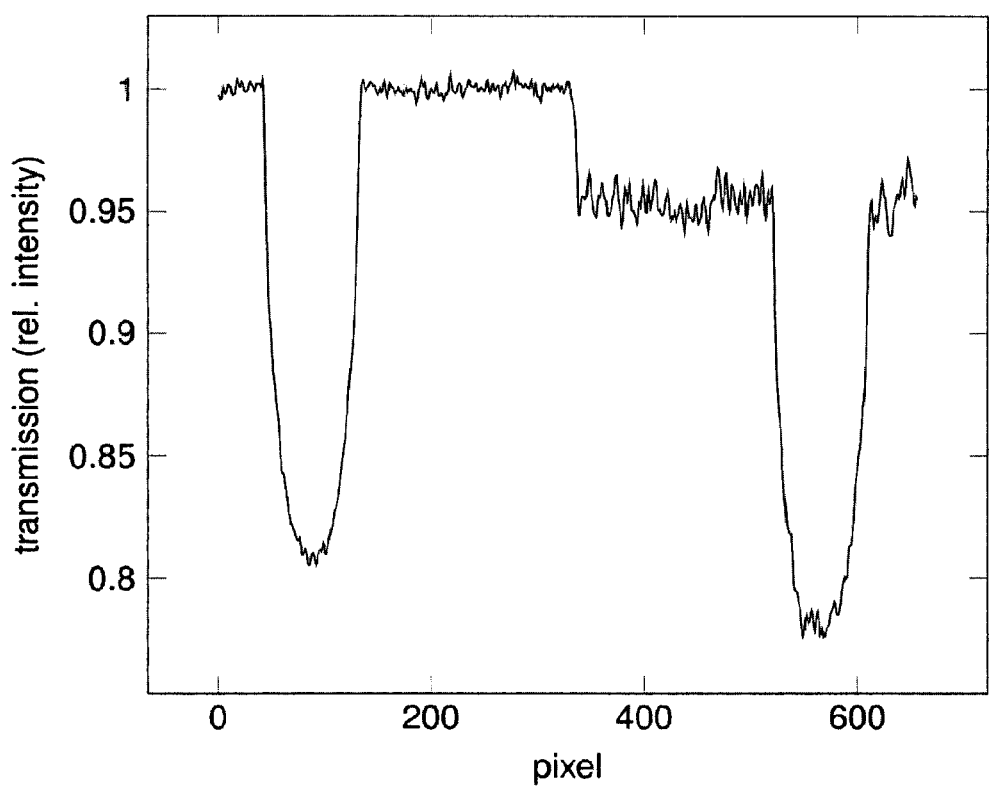
Figure 2B:
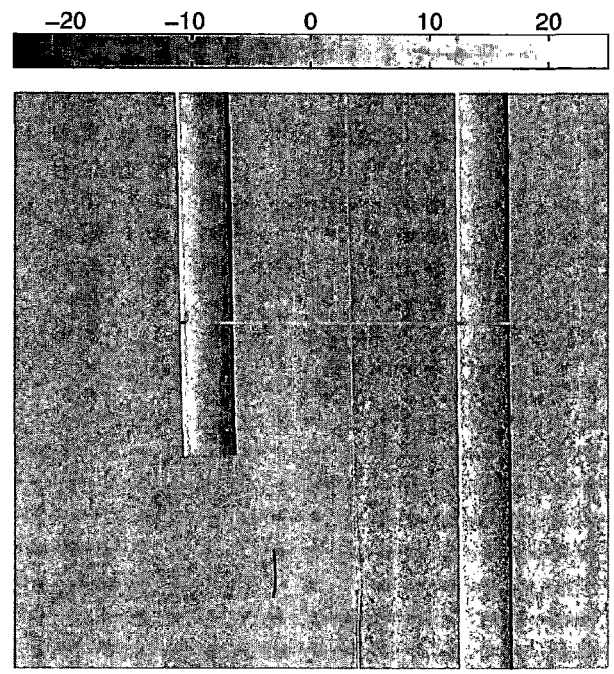
Figure 2E:
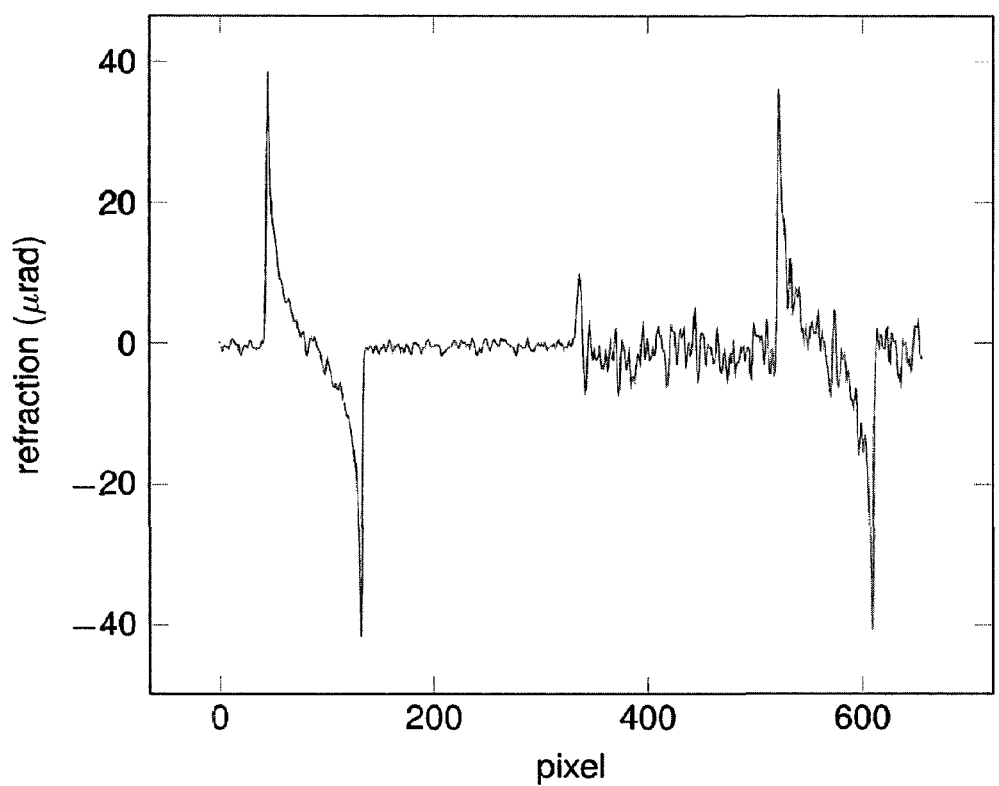
Figure 2C:
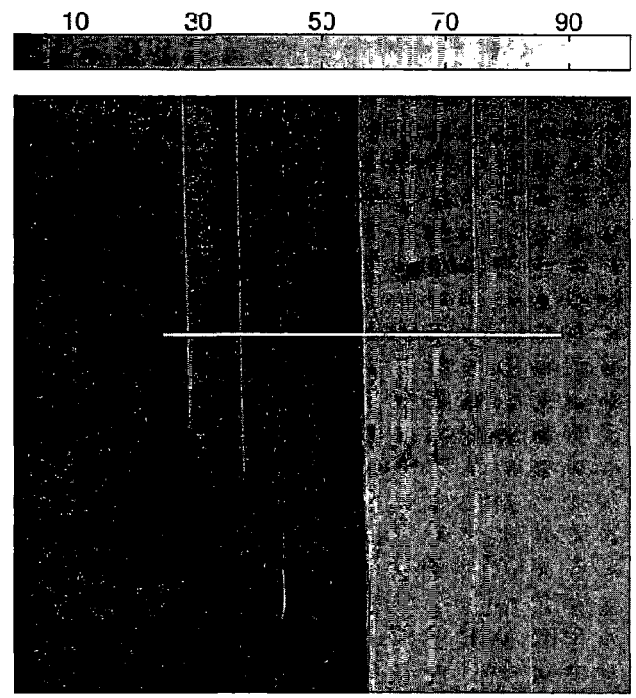
Figure 2F:
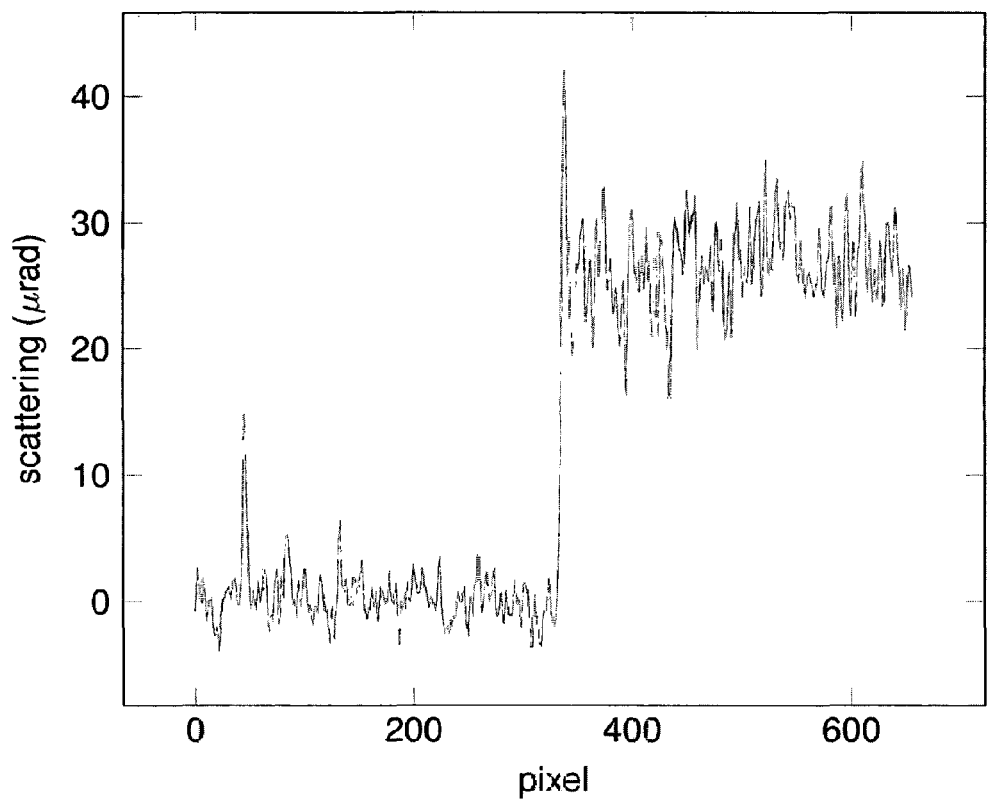

FIG. 1 illustrates schematic apparatus according to an embodiment of the invention. An X-ray source 2 emits X-rays which pass through slit apertures 32 in pre-sample mask 8, then through a sample 10 and slit apertures 34 in a detector mask 6. The slit apertures 32, 34 extend in the y direction perpendicular to the paper in FIG. 1. A detector 4 has multiple pixels 12 aligned with the apertures 34 in the detector mask. The detector 4 and detector mask 6 amount to a spatially resolving detector. By using a physical detector mask to provide the spatial resolution the resolution of the detector does not have to be particularly high.

Note that the pitch of the slit apertures 32, 34 in the two masks correspond, so that the spacing of X-ray beams 16 passing through the apertures 32 in the pre-sample mask 8 results in the beams corresponding to the apertures 34 in the detector mask. Alternative arrangements may include line skipped masks, so the lines in the pre-sample mask correspond for example in a 1:2 or other ratio to the lines in the detector mask 6.

Such apparatus is already described in WO2013/011317. However, WO2013/011317 teaches that the detector mask 6 is positioned in specific positions with respect to pre-sample mask 8 at pixel level.

In the present case, these positions are less constrained and measurement proceeds as will now be described.

The detector mask is displaced by an amount $\bar{x}$ with respect to the sample mask. With respect to FIG. 1, the x direction corresponds to the vertical direction: the direction in the plane of the mask which is orthogonal to the apertures. This can be achieved by displacing either or both masks. In the embodiment used to generate the images presented in this application, this displacement is achieved by moving the sample mask in the plane of the mask.

Typically, the detector mask has apertures at a corresponding spacing to the pre-sample mask, in other words as imaged at the detector the spacing of the detector mask apparatus corresponds to the spacing of the pre-sample mask.

In this embodiment the image is imaged through a detector mask 6 and detector 4. In an alternative embodiment, the image is simply captured on a detector having a sufficiently high resolution (small pixels) and the image as would be recorded through a detector mask calculated by applying a suitable function to the captured image to calculate the image that would be achieved using a physical detector mask.

The advantage of using a physical detector mask is that the detector mask can provide the spatial resolution so the pixels of the detector can be larger. Larger pixels are particularly beneficial when imaging in medical applications which generally require low X-ray doses.

When the detector mask is displaced by an amount $\bar{x}$ with respect to the pre-sample mask, the intensity that reaches the detector plane can be written as:

$$\frac{I(\bar{x})}{I_0} = t(B_1 * S * O * B_2)(\bar{x} - \Delta x_R) \quad (1)$$

where * denotes convolution and $I_0$ is the beam intensity passing through the pre-sample aperture. In the set-up of this embodiment, the apertures are oriented along the y direction, which results in phase/dark field sensitivity along the x direction. For this reason we discuss a one-dimensional problem in x, assuming the different rows of pixels independent one from each other. The fraction of the beam intensity transmitted through the sample is represented by t, $B_1(x)$ indicates the point-source (i.e., un-blurred) image of the pre-sample aperture, $S(x)$ represents the source distribution projected at the detector mask plane, $O(x)$ is the function describing the scattering (beam broadening) introduced by the sample and $B_2(x)$ is the point source image of the detector mask. For the case in which the masks have perfect non-transmitting apertures, one could write $B_1 = (1/Gb_1)\mathrm{rect}(x/Gb_1)$ and $B_2 = \mathrm{rect}(x/b_2)$, where $b_1$ and $b_2$ are the width of the pre-sample mask and detector mask apertures, respectively, rect(x) is the rectangular function defined as 1 for $-½<x<½$ and 0 elsewhere, and G is the geometrical magnification factor.

The function $O(x)$, with which the scattering (dark field) is described, could be ideally thought of as the detector-plane distribution of a pencil beam hitting a purely scattering object.

In the presence of refraction, the detector aperture $B_2$ appears shifted by an amount $\Delta x_R = \Delta \theta_R z_{od}$ with respect to the beam, as a consequence of the local deflection of the beam by an angle $\Delta \theta_R$ caused by the sample-induced refraction ($z_{od}$ is the object-detector distance). This angle is directly proportional to the gradient of the phase shift $\Phi(x,y)$ induced by the sample: i.e. $\Delta \theta_R = (\lambda/2\pi)(\partial\Phi(x,y)/\partial x)$, where $\lambda$ is the radiation wavelength. By exchanging the order of the convolutions in Eq. 1, one obtains:

$$\frac{I(x)}{I_0} = t(O * L)(x - \Delta x_R) \quad (2)$$

where the illumination function $L(x)$ describes how the detected beam intensity changes as a function of the relative displacement x between the pre-sample and the detector mask, in the absence of the sample.

Assuming that L and O can be expressed as a summation of Gaussian functions, i.e.

$$L(x) = \sum_{n=1}^{N} \left(A_n / \sqrt{2\pi\sigma_n^2}\right)\exp\left[-\frac{(x - \mu_n)^2}{2\sigma_n^2}\right]$$

and $$O(x) = \sum_{m=1}^{M} \left(A_m / \sqrt{2\pi\sigma_m^2}\right)\exp\left[-\frac{(x - \mu_m)^2}{2\sigma_m^2}\right],$$

Eq. 2 can be written explicitly as:

$$\frac{I(x)}{I_0} = t \sum_{m=1}^{M} \sum_{n=1}^{N} A_{mn} \exp\left[-\frac{(x - \mu_{mn})^2}{2\sigma_{mn}^2}\right] \quad (3)$$

where $\mu_{mn} = \mu_m + \mu_n$, $\sigma_{mn}^2 = \sigma_m^2 + \sigma_n^2$ and $A_{mn} = A_m A_n (1/\sqrt{2\pi\sigma_{mn}^2})$. The mean of the single Gaussian function terms is indicated with $\mu$, their variance with $\sigma^2$ and their amplitude with A; the number of values of m is M and the number of values of n is N.

This forms the basis for a system of equations that can be solved analytically by using only three projection images, and enables the separate reconstruction of the transmission, refraction and scattering properties of the sample. While transmission and refraction are quantities that are normally averaged over lengths of the order of the pixel size, scattering is related to fluctuations on a much shorter (sub-pixel) scale, and therefore reveals properties of the sample that are complementary to those given by the other two quantities.

In the case N=1, M=1, the only values of m and n are 1 and so the sum in equation (3) has only one term.

Consider three images acquired with relative displacement of the masks of $x_1$, $x_3 = -x_1$ (i.e. two arbitrarily chosen symmetric position around the maximum of $L(x)$) and $X_2 = 0$ (the maximum itself), Eq. 3 can be arranged in the system:

$$I_1 = t \frac{A_{MN}}{\sqrt{2\pi\sigma_{MN}^2}} \exp\left[-\frac{(x_1 - \Delta x_R)^2}{2\sigma_{MN}^2}\right] \quad (4)$$

$$I_2 = t \frac{A_{MN}}{\sqrt{2\pi\sigma_{MN}^2}} \exp\left[-\frac{(-\Delta x_R)^2}{2\sigma_{MN}^2}\right] \quad (5)$$

$$I_3 = t \frac{A_{MN}}{\sqrt{2\pi\sigma_{MN}^2}} \exp\left[-\frac{(-x_1 - \Delta x_R)^2}{2\sigma_{MN}^2}\right] \quad (6)$$

These equations can be solved for t, $\Delta x_R$ and $\sigma_M^2$ $$t = \frac{1}{A_{MN}} \sqrt{4\pi\left(\frac{x_1^2}{D+C}\right)} I_2 \exp\left[\frac{1}{2^4}\frac{(D-C)^2}{D+C}\right] \quad (7)$$

$$\Delta x_R = \frac{x_1}{2}\frac{D-C}{D+C} \quad (8)$$

$$\sigma_M^2 = \frac{2x_1^2}{D+C} - \sigma_N^2 \quad (9)$$

with $$C = -2\ln\left(\frac{I_1}{I_2}\right)$$

and $$D = -2\ln\left(\frac{I_3}{I_2}\right)$$

and $\sigma_N^2$ is the variance of the Gaussian representing the illumination function L(x).

This allows the separation of the contributions to $I_1$, $I_2$ and $I_3$ coming from absorption, refraction and scattering in the sample. It should be noted that limiting Equation (3) to the case N=1 and M=1 provides a reasonable approximation in a wide range of experimental conditions encountered in practice.

Thus, the method of the embodiment described is to first move the sample mask 8 in the x direction to a displacement $x_2$ that gives the maximum intensity measured on the detector 4. The image intensity measured in this position is $I_2$. Then, the sample mask 8 is moved to two further positions $x_1$ and $x_3$ where the further positions are symmetric around $x_2$ and the corresponding image intensity measured to give $I_1$ and $I_3$.

The closed form solutions of equations (4-9) apply to the case where the X-ray scattering and the illumination function can be described with a single Gaussian function. It is possible to relax this requirement and extract the unknown parameters from equation (3) numerically (for example by means of a fit). In this case also the requirements on the positions $x_i$, at which the images $I_i$ are acquired, are relaxed. If N>1 and M=1 (i.e. general illumination function L and single-Gaussian scattering function O) the minimum number of projection images to be acquired is still three. This includes all the practical cases in which the masks can be partially transmitting, the source distribution can be of any shape and also the apertures in the masks can have any profile.

It should be noted that, even if nothing or little is known about the imaging system, the illumination function L can be measured experimentally and fitted with an appropriate number of terms N. By numerically extracting the unknown parameters from equation (3) on a pixel by pixel basis, it is also possible to considerably relax the alignment requirements on the whole imaging system.

If an arbitrary scattering distribution O is used, this distribution can be approximated with a summation of Gaussian terms (M>1), and the minimum number of projection images would be equal to the number of unknown parameters in equation (3).

The calculation above for t, $\Delta x_R$ and $\sigma_M^2$ (equations 7 to 9) is carried out from the equations above for every pixel of the image and presented as three images, which will be referred to as the transmission, refraction and dark field image respectively. For completeness, we note that the dark field image presented in the Figures is the standard deviation $\sigma_M$ not its square $\sigma_M^2$.

If the masks are aligned, then the maximum intensity position is the same for each pixel. If the masks are misaligned, as discussed above, then a scan of one mask against the other can be carried out for each pixel so that the maximum intensity position is known for each pixel. In this case, the calculation may be a numerical solution of equation (2).

If it is known in advance that the sample has negligible or constant absorption, negligible refraction or negligible scattering, then equation 3 can be solved with only two images acquired, i.e. only two of $I_1$, $I_2$ and $I_3$.

Further, only a single image may be captured, at a general position x. Such an image will not allow quantitative use, but will display features with enhanced contrast compared with conventional radiography, in particular contain dark-field signal superimposed to conventional absorption signal and refraction signal. The relative amount of these contributions will vary depending on the sample and on the system. As an example, a single image acquired with a large displacement x will contain negligible refraction contrast, with absorption and scattering exhibiting inverted types of contrast. With an appropriately designed system, negligible refraction contributions could also be obtained for an image acquired at the maximum of the illumination curve L. In this case scattering and absorption would contribute with the same type of contrast and therefore the image would present enhanced features with respect to conventional radiography. Such implementation could be used as a fast method to distinguish between e.g. crystalline and amorphous materials such as explosives against harmless substances, or benign vs malignant breast calcifications.

Those skilled in the art will realize that the development over a basis of Gaussian functions appearing in equation (3) can be substituted with another basis.

Further, the hypothesis on the "Gaussianity" of the illumination curve (set-up dependent) may be relaxed, as may the constraint of the "Gaussianity" of the scattering function (sample dependent).

It is also possible to skip the step of developing such functions on a Gaussian basis (eq. 3) and solve eq. (2) directly, by means of numerical methods, which includes iteratively convolving the measured illumination function L with a desired scattering distribution. This could initially be a random guess for the function O, which would be convolved with L and compared with the measured curve. This would enable to correct the initial guess, and the process would then be iterated until satisfactory convergence is achieved. The transmission t and the refraction $\Delta x_R$ could be retrieved in a similar way.

In some cases, the masks used may have a non-negligible transmission and this may also be corrected for by taking into account transmission in the definition of L. This can be done by explicitly adding a constant term in the summation of Eq. 3, which would be a known parameter of the analytical form of equation (3) and the unknown parameters can be extracted as described above (for example by means of a fit). In addition, the effect of the transmission could also be left implicit and described with a Gaussian term having a very large standard deviation.

Further, as well as enabling the retrieval of the scattering signal, the method can also be applied to retrieve the phase at arbitrary illumination level. This practically means that one can perform quantitative differential phase imaging at different levels of sensitivity, which is a generalization of the previous work of Peter Munro (patent application GB1112537.4, 21 Jul. 2011).

Optimum illumination levels depend on the application (e.g. if dose, time or detector is the dominant constraint).

As an alternative, the three quantities (absorption, refraction and scattering) can also be measured by placing just one mask in front of the sample and using a high resolution detector (e.g. ~1 micron). In this way the change in the shape and position of the beam can be measured directly. This method would require a single shot per illuminated area of the sample. In this case, the spatial resolution of the detector system is achieved not using a mask but using the inherent resolution of the detector.

Finally, an asymmetric pre-sample mask can be used to acquire all illumination levels described above in a single shot on different (e.g. alternating) pixel columns/rows (or even individual pixel): this would allow a single shot quantitative retrieval of the above quantities by sacrificing some spatial resolution. This type of masks could also be used in a scanning system where the sample is scanned across a two (or three or more) asymmetric slits system and the images $I_i$ are simultaneously acquired.

As a preliminary demonstration of the different properties of these three signals, an image of acrylic cylinders and a paper step wedge is shown in FIG. 2. In the transmission image (2(a)), the three acrylic cylinders appear with the same contrast, regardless of their orientation. The refraction image (2(b)) reveals a strong differential phase contrast for the two vertical cylinders, while the one which is almost horizontal has a very weak signal, except at its vertical edge where the cylinder itself terminates. In the scattering image (2(c)), the microscopic structure of the paper layers is revealed, while the acrylic, which has negligible density variation at microscopic length scales, vanishes.

Figure 3:
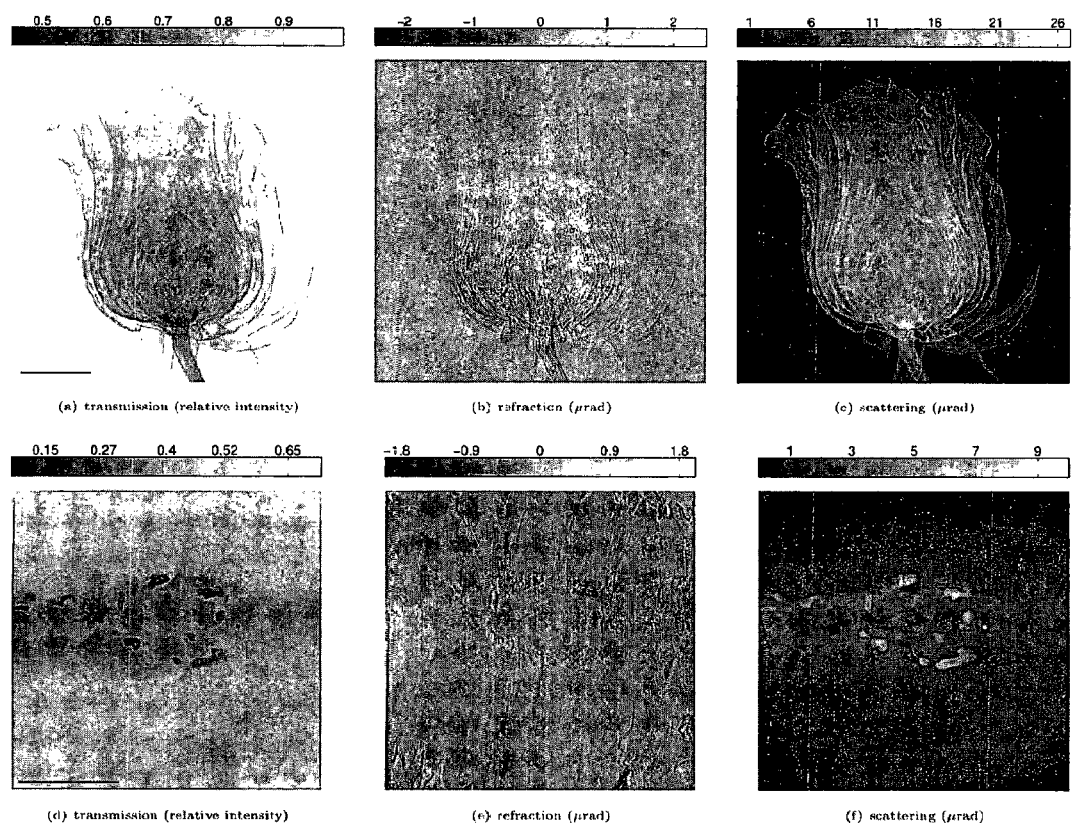
FIG. 3 shows further images captured in accordance with an embodiment of the invention.

In addition to this demonstration on a geometric phantom, we present example images of two biological samples (FIG. 3). The images of a rose (3a transmission, 3b refraction and 3c scattering) clearly demonstrate the complementarity of the three signals, and the images of a breast tissue sample (3d transmission, 3e refraction and 3f scattering) are also shown to indicate a first example of possible application.

The total entrance dose required to collect the full set of three images was of 12 mGy, compatible with the limits imposed by clinical practice. Similar images were recently presented by Stampanoni et al, who also demonstrated their advantages in terms of diagnostic potential. However, due to the different phase imaging method employed in that case, a radiation dose at least one order of magnitude above clinical limits was required, while the method proposed here would be readily compatible with clinical requirements.

All the images were acquired with an amorphous Selenium flat panel with a pixel pitch of 85×85 μm. The X-ray source was a rotating anode, Molybdenum target X-ray tube operated at 35 kV and 25 mA with an apparent spot size of 75 μm full width half maximum. The masks were aligned with a stack of translation stages and swivel stages. The sample mask pitch and aperture were $p_1$=66.8 μm and $b_1$=12 μm, while for the detector mask they were $p_2$=83.5 μm and $b_2$=20 μm, respectively. For this specific set-up, the absorbing septa in the masks where made of gold on a graphite substrate. However other choices of material are possible both for the transmitting and absorbing parts, including partially transmitting septa.

The gold thickness was approximately 30 μm on a graphite substrate, with a field of view of 4.8–4.8 cm. The source to detector distance was 2 m and the object to detector distance $z_{od}$=40 cm.

Acrylic cylinders used for the phantom in FIG. 2 had a diameter of 3 mm and a density of 1.2 g/cm3.

The breast tissue sample was approximately 2 cm thick and was obtained from mastectomies after informed consent; the study was approved by the local ethical regulatory bodies. For imaging of this specimen a filtration of 30 μm of Molybdenum was used. Entrance doses were directly measured with a calibrated ionization chamber and with TLD, stated values refer to the average of those two measures.

Those skilled in the art will realise that several alternatives exist to the detailed embodiments discussed above.

For example, equation 2 is a representation of scattering, transmission and refraction obtained starting from geometrical optics principles. Those skilled in the art will realise that the same, or an equivalent formulation can be obtained starting from a different model, for example wave optics/diffraction integrals.

The invention claimed is:

1. A method of X-ray imaging, comprising:
   passing an X-ray beam through an absorbing pre-sample mask with one or more apertures spaced apart in the x direction;
   passing the X-ray beam through a sample;
   detecting the X-rays using a spatially resolving detector representing a detector mask having one or more apertures spaced apart in the x-direction at a corresponding spacing to the apertures in the pre-sample mask, to provide one or more images $I_i$, wherein i is the number of images with the relative position of the pre-sample mask and detector mask at respective position or positions $x_i$, wherein i is the number of positions and
   obtaining a dark field image of the sample by calculating the dark field image from the captured image or images $I_i$ at respective positions $x_i$
   using a formulation representing the image intensity as a function of scattering, transmission and refraction, wherein obtaining a dark field image comprises solving the equation $$\frac{I(x)}{I_0} = t(O * L)(x - \Delta x_R)$$

from the captured image or images Ii at respective positions $x_i$ to obtain the dark field image of the sample;
   where * denotes convolution, $I_0$ is the beam intensity passing through the sample aperture, the illumination function L(x) describes how the detected beam intensity changes as a function of the relative displacement x between the pre-sample and the detector mask, in the absence of the sample, t represents the transmission of the sample, $\Delta x_R$ represents the refraction induced by the sample and O(x) describes the scattering of the sample, represented in the dark field image.

2. The method according to claim 1, wherein the step of detecting the X-rays provides at least two images $I_1$, and $I_2$ with the relative position of the pre-sample mask and detector mask at least two respective positions $x_1$, and $x_2$;
   further comprising calculating a transmission image of the sample, and/or a the refraction image of the sample from the captured images in addition to the dark field image.

3. The method according to claim 2 further comprising measuring L pixel by pixel and using the measured value of L for each pixel when solving the equation from the captured image to calculate at least two of the transmission image, the refraction image and the dark field images.

4. The method according to claim 2, wherein the step of calculating the images includes solving:

$$\frac{I(x)}{I_0} = t \sum_{m=1}^{M} \sum_{n=1}^{N} A_{mn} \exp\left[-\frac{(x-\mu_{mn})^2}{2\sigma_{mn}^2}\right]$$

wherein the scattering O is represented by a sum of M Gaussian functions and the illumination function L is represented by the sum of N Gaussian functions, $\sigma_{mn}^2 = \sigma_m^2 + \sigma_n^2$, $\sigma_m^2$ is the variance of the m-th Gaussian function describing the scattering U caused by the sample, $\sigma_n^2$ is the variance of the n-th Gaussian function describing the illumination function L, $A_{mn} = A_m A_n (1/\sqrt{2\pi\sigma_{mn}^2})$, with $A_m$ and $A_n$ the scalars representing the amplitudes of the Gaussian distributions.

5. The method according to claim 4, wherein $x_3 = x_1$, $M = N = 1$ and the step of calculating at least two of a transmission image t of the sample, a refraction image $\Delta x_R$ of the sample and a scattering image $\sigma_M^2$ of the sample solve:

$$I_1 = t \frac{A_{MN}}{\sqrt{2\pi\sigma_{MN}^2}} \exp\left[-\frac{(x_1 - \Delta x_R)^2}{2\sigma_{MN}^2}\right] \quad (4)$$

$$I_2 = t \frac{A_{MN}}{\sqrt{2\pi\sigma_{MN}^2}} \exp\left[-\frac{(-\Delta x_R)^2}{2\sigma_{MN}^2}\right] \quad (5)$$

$$I_3 = t \frac{A_{MN}}{\sqrt{2\pi\sigma_{MN}^2}} \exp\left[-\frac{(-x_1 - \Delta x_R)^2}{2\sigma_{MN}^2}\right] \quad (6)$$

wherein $\sigma_{MN}^2 = \sigma_M^2 + \sigma_N^2$, and $\sigma_M^2$ is the variance of the Gaussian function describing the scattering caused by the sample, and $\sigma_N^2$ is the variance of the Gaussian function describing the illumination curve L, $A_{MN} = A_M A_N (1/\sqrt{2\pi\sigma_{MN}^2})$, with $A_M$ and $A_N$ the scalars representing the amplitudes of the respective Gaussian distributions.

6. The method according to claim 4 wherein the transmission image t is calculated using $$t = \frac{1}{A_{MN}} \sqrt{4\pi \left(\frac{x_1^2}{D+C}\right)} I_2 \exp\left[\frac{1}{2^4} \frac{(D-C)^2}{D+C}\right] \quad (7)$$

with $$C = -2 \ln\left(\frac{I_1}{I_2}\right)$$

and $$D = -2 \ln\left(\frac{I_3}{I_2}\right).$$

7. The method according to claim 4 wherein the refraction image $\Delta x_R$ is calculated using:

$$\Delta x_R = \frac{x_1}{2} \frac{D-C}{D+C} \quad (8)$$

with $$C = -2 \ln\left(\frac{I_1}{I_2}\right)$$

and $$D = -2 \ln\left(\frac{I_3}{I_2}\right).$$

8. The method according to claim 4 wherein the scattering image $\sigma_M^2$ is calculated using:

$$\sigma_M^2 = \frac{2x_1^2}{D+C} - \sigma_N^2 \quad (9)$$

with $$C = -2 \ln\left(\frac{I_1}{I_2}\right)$$

and $$D = -2 \ln\left(\frac{I_3}{I_2}\right)$$

and $\sigma_N^2$ is the variance of the Gaussian representing the illumination function L.

9. The method according to claim 2 wherein at least one of the pre-sample mask and detector mask is asymmetric, having at least two slits, in order to image the sample simultaneously at different values of L, the method further comprising retrieving a plurality of images with a single exposure.

10. The method according to claim 2 wherein at least one of the pre-sample mask and detector mask is asymmetric, having at least two slits, in order to image the sample simultaneously at different values of L, the method comprising scanning the sample and retrieving the three images.

11. The method according to claim 1, wherein the step of obtaining a dark field image of the sample comprises solving numerically the formulation representing the image intensity.

12. The method according to claim 1, further comprising identifying the maximum position $x_2 = 0$ with the maximum intensity of X-rays detected on the detector,
moving the detector mask with respect to the sample mask in the x direction to at least one of positions $x_1$ and $x_3$ on either side of the maximum position $x_2$;
capturing at least two of an image $I_2$ at the maximum position $x_2 = 0$ and respective images $I_1$ and $I_3$ at the respective positions $x_1$ and $x_3$; and
calculating at least two of a transmission image t of the sample, a refraction image of the sample and a dark field image of the sample from $I_1$, $I_2$ and $I_3$.

13. The method according to claim 12 wherein the respective positions $x_1$ and $x_3$ are equally spaced on opposite sides of the maximum position $x_2 = 0$ so that $x_3 = -x_1$.

14. The method according to claim 1, wherein each of the images $I_1$, $I_2$ and $I_3$ are captured and each of the transmission image of the sample, the refraction image of the sample and the dark field of the sample are calculated from $I_1$ $I_2$ and $I_2$.

15. The method according to claim 1, wherein
two of the images $I_1$, $I_2$ and $I_3$ are captured, one of the transmission image t of the sample, the refraction image $\Delta x_R$ of the sample and the scattering image $\sigma_M^2$ of the sample is assumed to be zero or constant and
the others of the transmission image t of the sample, the refraction image $\Delta x_R$ of the sample and the scattering image $\sigma_M^2$ of the sample are calculated from the two captured image and the image assumed to be zero.

16. The method according to claim 1, including representing the illumination function L by a plurality of Gaussian functions.

17. The method according to claim 1, wherein the step of detecting the X-rays using a spatially resolving detector passes the X-rays through a physical detector mask having a plurality of apertures spaced apart in the x-direction at a corresponding spacing to the apertures in the pre-sample mask onto a detector.

18. The method according to claim 1, wherein the step of detecting the X-rays using a spatially resolving detector captures an image of the X-rays on a spatially resolving detector and calculates at least one image or images representing the captured image imaged through a detector mask having a plurality of apertures spaced apart in the x-direction at a corresponding spacing to the apertures in the pre-sample mask, with the relative position of the pre-sample mask and detector mask at respective position or positions $x_i$, wherein i is the number of positions.

19. A method of X-ray imaging, comprising:
passing an X-ray beam through an absorbing pre-sample mask with a plurality of apertures spaced apart in the x direction;
passing the X-ray beam through a sample;
detecting the X-rays passing through the sample on an X-ray detector to provide at least one image of the sample, including the intensity at different offsets x from the centre of the image of each of the plurality of apertures;
and solving the equation $$\frac{I(x)}{I_0} = t(O * L)(x - \Delta x_R)$$

from the captured image or images $I_1$, $I_2$ measured at different offsets from the image of the apertures on the detector
where * denotes convolution, $I_0$ is the beam intensity passing through the sample aperture, the illumination function L(x) describes how the detected beam intensity changes as a function of the relative displacement x between the pre-sample and the detector mask, in the absence of the sample, t represents the transmission of the sample, $\Delta x_R$ represents a refraction image of the sample and O(x) represents the scattering of the sample.

20. A computer program product adapted to calculate a dark field image from at least one image $I_i$ wherein i is the number of images recorded by passing an X-ray beam through an absorbing pre-sample mask with a plurality of apertures spaced apart in the x direction, through a sample, and using a spatially resolving detector representing a detector mask having a plurality of apertures spaced apart in the x-direction at a corresponding spacing to the apertures in the pre-sample mask with the relative position of the pre-sample mask and detector mask at respective position or positions $x_i$ wherein i is the number of positions;
wherein the computer program product is arranged to obtain a dark field image of the sample by calculating the dark field image from the captured image or images I at respective positions x using a formulation representing the image intensity as a function of scattering, transmission and refraction.

21. A computer program product adapted to calculate a dark field image from at least one image $I_i$ wherein i is the number of images recorded by passing an X-ray beam through an absorbing pre-sample mask with a plurality of apertures spaced apart in the x direction, through a sample, and using a spatially resolving detector representing a detector mask having a plurality of apertures spaced apart in the x-direction at a corresponding spacing to the apertures in the pre-sample mask with the relative position of the pre-sample mask and detector mask at respective position or positions $x_i$ wherein i is the number of positions;
wherein the computer program product is arranged to solve the equation $$\frac{I(x)}{I_0} = t(O * L)(x - \Delta x_R)$$

from the captured image or images I at respective positions x to obtain the dark field image of the sample;
where * denotes convolution, $I_0$ is the beam intensity passing through the sample aperture, the illumination function L(x) describes how the detected beam intensity changes as a function of the relative displacement x between the pre-sample and the detector mask, in the absence of the sample, t represents the transmission of the sample, $\Delta x_R$ represents the refraction induced by the sample and O(x) represents the scattering of the sample, represented in the dark field image.

* * * * *